United States Patent [19]

Besic

[11] 4,405,600
[45] Sep. 20, 1983

[54] METHODS AND MATERIALS FOR PREVENTION OF CARIOUS DEGRADATION OF TEETH

[75] Inventor: Frank C. Besic, Manitowoc, Wis.

[73] Assignee: University Patents, Inc., Norwalk, Conn.

[21] Appl. No.: 139,199

[22] Filed: Apr. 11, 1980

Related U.S. Application Data

[63] Continuation-in-part of Ser. No. 46,314, Jun. 7, 1979, abandoned.

[51] Int. Cl.³ ............................................... A23K 1/16
[52] U.S. Cl. ...................................... 424/57; 127/29; 127/30; 424/49; 424/154; 426/658
[58] Field of Search ................... 127/29, 30; 426/658; 424/49, 57, 154

[56] References Cited

U.S. PATENT DOCUMENTS

| | | |
|---|---|---|
| 2,967,131 | 1/1961 | Elbreder et al. . |
| 3,194,682 | 7/1965 | Tippens et al. . |
| 3,337,412 | 8/1967 | Elbreder . |
| 3,375,168 | 3/1968 | Curtin et al. . |
| 3,462,366 | 8/1969 | Luoma . |
| 3,467,529 | 9/1969 | Muhler . |
| 3,469,989 | 9/1969 | Gagolski et al. . |
| 3,471,613 | 10/1969 | Gagolski et al. . |
| 3,836,396 | 9/1974 | McNamara ............................. 127/30 |
| 3,914,410 | 10/1975 | Godfrey ................................. 127/30 |
| 4,022,887 | 5/1977 | Harris et al. . |
| 4,048,299 | 9/1977 | Litchfield ............................. 424/49 |
| 4,048,300 | 9/1977 | Tomlinson et al. . |
| 4,080,440 | 3/1978 | Di Giulio et al. . |
| 4,083,955 | 4/1978 | Grabenstetter . |
| 4,097,588 | 6/1978 | Levine . |
| 4,108,980 | 8/1978 | Duff ................................. 424/57 X |
| 4,127,645 | 11/1978 | Witzel . |
| 4,177,258 | 12/1979 | Gaffar . |
| 4,183,915 | 1/1980 | Gaffar . |
| 4,193,988 | 3/1980 | Forward . |
| 4,228,150 | 10/1980 | Robyt ............................. 426/658 X |
| 4,234,608 | 11/1980 | Linehan ........................... 426/658 X |
| 4,267,167 | 5/1981 | Weitzman ......................... 424/57 X |
| 4,279,931 | 7/1981 | Verwaerde ....................... 426/658 X |
| 4,323,551 | 4/1982 | Parran ............................. 424/57 X |

FOREIGN PATENT DOCUMENTS

| | | |
|---|---|---|
| 256211 | 7/1964 | Australia . |
| 259269 | 9/1964 | Australia . |
| 261082 | 1/1964 | Australia . |
| 290459 | 5/1967 | Australia . |
| 445260 | 1/1971 | Australia . |
| 1009957 | 11/1965 | United Kingdom . |
| 1384375 | 2/1975 | United Kingdom . |
| 1408922 | 10/1975 | United Kingdom . |

OTHER PUBLICATIONS

B. G. Bibby et al., J. Dent. Res., 49, 1481–1486 (1976).
Abstract, J. Dent. Res., 55, Special Issue B, p. B126, Mundorff and Bibby, 1976.
B. M. Shrestha et al., Caries Res., 16, 12–17 (1982).
B. M. Shrestha, Master's Thesis entitled, "In Vitro Chemical Effect of Different Fluoride and Non-Fluoride Compounds on Enamel Solubility," Eastman Dental Center, The University of Rochester, Rochester, NY, 1970.
Grenby, "Trials of Three Organic Phosphorous Containing Compounds as Protective Agents Against Dental Caries in Rats," J. Dent. Res., 52(3), 454–461, May–Jun. 1973.
Chemical Abstracts, 53:15347a (1959).
Chemical Abstracts, 82:160119s (1975).
McClure et al., Rev. 1960 Dent. Res., 62, pp. 25/511–29/515 (1961).
McClure et al., J. Am. Dent. Assn., 58, pp. 36–41 (1959).
Grenby, "The Control of Dental Decay," Chemistry and Industry, pp. 166–171, 2/15/75.
Grenby et al., "Control of Dental Decay," Chemistry and Industry, p. 921, 11/1/75.
Grenby, "Tests of Calcium Surcrose Phosphate as a Protective Agent Against Dental Caries in Rats and In Vitro," J. Dent. Res. 50(5), p. 1213, Sep.–Oct. 1971.

*Primary Examiner*—Sidney Marantz
*Attorney, Agent, or Firm*—Merriam, Marshall & Bicknell

[57] ABSTRACT

Cariogenic substances such as foodstuffs are treated to incorporate a soluble source of calcium or phosphate ions to provide a product of calcium and phosphate ion concentrations in fluids of salivary retention areas preclusive of carious dissolution of dental enamel. In nonaqueous foodstuffs, the calcium or phosphate ion source should be at least as rapidly soluble as cariogenic, e.g., carbohydrate, components therein. Also provided are mouth rinse solutions comprising a soluble source of calcium or phosphate ions and an osmotically active agent effective in delivering such ions to fluids trapped in salivary retention areas.

16 Claims, 1 Drawing Figure

METHODS AND MATERIALS FOR PREVENTION OF CARIOUS DEGRADATION OF TEETH

This is a continuation-in-part of my co-pending U.S. application Ser. No. 46,314, filed June 7, 1979 now abandoned.

BACKGROUND

The present invention relates generally to prevention of dental caries and more specifically provides: methods for lessening the cariogenicity of materials to be placed in the oral cavity; products, especially foodstuffs, treated according to such methods to have substantially diminished cariogenic effects when taken into the mouth; and methods and materials for treating the oral cavity to counteract or neutralize the effects of cariogenic materials present in salivary retention areas.

The incidence of dental caries is pandemic, resulting in enormous discomfort to dental patients and huge expenditures of monetary resources. The prior art is rich in proposals for prophylactic and restorative treatments respecting carious degradation of teeth. Such treatments may be grossly classified into two groups, (1) "localized" applications of materials directly to the mouth, and (2) "systemic" (generally dietary) treatments. Both groups of treatments focus on preserving the integrity of crystalline minerals from which the teeth are formed and consequently there often exists a degree of similarity in treating agents employed.

"Localized" treatments generally consist either of routine application of dental preparations (toothpastes, mouthwashes, and the like) which contain relatively dilute concentrations of various soluble and insoluble agents, or periodic administration of similar substances in more concentrated form. A first type of routine treatment has as its goal the reduction of population of flora and consists of application of bactericidal or bacteriostatic agents. Such treatments are not pertinent to the present invention.

Toothpastes routinely employed in the art may consist simply of abrasive materials whose function is to wear away dental plaque (see, e.g., U.S. Pat. No. 3,629,398), but more often toothpastes contain a wide variety of elements in combinations substantially duplicating the mineral content of the teeth. U.S. Pat. No. 4,048,300, for example, discloses dental creams containing, inter alia, abrasive minerals. The asserted function of such dental creams is to provide not only a source of plaque-removing abrasives, but also to topically "remineralize" exposed tooth surfaces which may have been selectively demineralized in early stages of caries formation. Many toothpastes include fluoride ion sources in low concentrations (see, e.g., U.S. Pat. No. 3,885,028) and recent reports have indicated that use of mouthwashes comprising a 0.2 percent solution of sodium fluoride is effective in reducing the incidence of dental caries in children.

The most common long-term periodic treatments are also aimed at "remineralization" and involve applying concentrated solutions and suspensions of one or more of the twenty-one elements ordinarily present in the tooth itself. Especially preferred treatments include fluorine salts or calcium and phosphate ion sources. U.S. Pat. No. 4,083,955, for example, discloses allegedly beneficial remineralization processes involving sequential application of separate compositions providing calcium ions or phosphate ions. U.S. Pat. No. 4,080,440 discloses application of a metastable, low pH, mixture of soluble sources of calcium and phosphate ions which preferably contains a source of fluorine ions. Both these types of applications specifically acknowledge a basic problem inherent in locally supplying calcium and phosphate ions to the tooth surface, i.e., the rapid formation of relatively insoluble (and ineffective) calcium phosphate or calcium fluoride salts upon admixing ion sources in solution. As another example, U.S. Pat. No. 3,978,206 discloses dental products and appliances made with ion exchange resins containing calcium, phosphate and fluorine ions, which resins are said to bypass the calcium phosphate and/or calcium fluoride precipitation problem.

"Systemic" treatments of the prior art are frequently aimed at maintaining and/or elevating "whole body" levels of calcium, phosphorous, fluorine and other elements in order to directly or indirectly provide an enhanced storehouse of materials for natural mineralization and, assertedly, remineralization of teeth. Treatment of water supplies to provide a dietary intake of fluorine on the order of one-half to one part per million is generally acknowledged as producing salutory cariostatic effects on children during the years of permanent tooth formation. Once teeth have been fully formed, however, such systemic fluoride treatments are generally held to be ineffective in preventing caries and, despite immense research efforts, the mechanism of action of fluorine in retarding tooth decay remains unclear.

Substantial efforts in the prior art have also been directed toward supplementing dietary intake of calcium, phosphorous and other elements, for the purpose of providing long term cariostatic effects. See, e.g., Limbustu, et al., *J.D. Res.*, 39, No. 4, p.722 (1960); Dalderup, *J.D. Res.*, 38, No. 6, pp. 1173-7 (1959); McClure, et al., *J.D. Res.*, 38, No. 4, pp. 776-781 (1959); and McClure, et al., *J.A.D.A.*, 58, pp. 36-41 (1959). Wynn, et al., *J.D. Res.*, 39, No. 6, pp. 1148-1151 (1960) provides an excellent analysis of prior experimental studies on the cariostatic effects of various calcium and phosphorous supplemented diets, concluding the results are frequently contradictory for wholly unexplainable reasons. See also, Limbasuta, "Studies on the Prevention of Experimental Dental Caries in Rats with Calcium, Phosphate and Fluoride Compounds", M.S. Thesis, The University of Rochester, Rochester, N.Y., 1961.

The published literature in this area is currently said to contain over 100 reports of caries preventative action resulting from increased intake by experimental animals of phosphates, alone and in combination with other metal ions (including calcium) as well as in combination with a source of fluorine. Systemically administered phosphates are said to differ in cariostatic activity depending on the type of anion (cyclictrimeta-, hexameta-, ortho-, and pyrophosphate, increasing in effectiveness in that order). Compounds of the same phosphate series are also said to vary in activity depending on the cation (hydrogen, sodium, potassium, ammonium, calcium and magnesium, decreasing in that order. The more pertinent studies of this type have indicated that cariostatic effects of phosphates appeared to be due in part to direct action of phosphate on the teeth as food passes through the mouth, as well as to the return of phosphate to the mouth as a salivary constituent. See, "Minerals: Calcium and Phosphorus" by R. S. Harris, appearing in "Dietary Chemicals vs. Dental Caries" Advances in Chemistry Series, 94, at pp. 116-122 (American Chemical Society, Washington, D.C. 1970).

Also pertinent to the background of the invention are prior art proposals for solubilization of normally insoluble phosphates to facilitate their transport and utilization in biological systems. U.S. Pat. Nos. 3,375,168 and 3,494,916, for example, are directed to methods for forming solubilized complexes of sugars and inorganic phosphates. Such complexes are said to be useful both in remineralization of teeth (when incorporated in toothpastes) and as components as cariostatic diets. As another example, U.S. Pat. No. 4,022,887 treats the preparation of edible cyclotriphosphates and cyclotetraphosphates and their asserted use as phosphorous supplements in caries-inhibiting diets.

The above-noted prior art developments have unfortunately resulted in only minor advances in prevention of carious degradation of teeth. To date, none of the alleged short term or long term "remineralization" processes has been shown to be consistently effective and, with the possible exception of water fluoridation, none of the proposed dietary supplementation schemes has uniformly resulted in significant reduction in the incidence of dental caries. Indeed, in many instances the proposed methods and materials have proven to have deleterious side effects. Long term exposure to water having fluorine levels of ten parts per million or more results in mottling of teeth. Indeed, great care must be taken in administering concentrated sodium and stannous fluoride to teeth in order to avoid poisoning of the patient.

As further background to the present invention it is to be noted that dental enamel (the hard, glistening substance covering the exposed portions of the teeth) is composed chiefly of hydroxypatite with small amounts of carbonate, magnesium, fluoride and an organic matrix (about 0.5 percent) of glycoprotein and a keratin-like protein. Structurally, enamel is made up of oriented rods, each of which consists of a stack of rodlets encased in an organic prism sheath. Carious dental enamel is generally recognized to result from the selective dissolution of apatite crystallites of varying size and shape.

In vitro model studies by the inventor and his co-workers have established that the selective demineralization of intact enamel resembling in vivo dental caries is accomplished not simply by acid treatment but by, e.g., exposure to aqueous inorganic and organic acid solutions which are less than fully saturated with calcium and phosphate ions.

The dissolution/demineralization process in such systems is generally seen to continue until the acid medium in contact with the tooth surface becomes essentially saturated with dissolved calcium and phosphate ions, whereupon dissolution ceases unless events occur which again bring about a relative unsaturation of the aqueous medium. If, for example, it occurs that the acidity of the medium is increased (either by addition of hydrogen ions directly or by formation of hydrogen ions by salivary flora) the demineralization process will again be initiated. Within this context one can envision the following model of the events leading up to carious degradation of enamel surfaces.

In the oral cavity, enamel surfaces are continuously bathed with salivary fluid which normally has a pH within the range of 6.5 to 7.5 and is essentially saturated with calcium ions (about 0.058 mg/ml) and phosphate ions (about 0.168 mg/ml). No dissolution of enamel will ordinarily occur unless the pH of the saliva in direct contact with the tooth surface is reduced, resulting in relative unsaturation with calcium and phosphate ions. Decreases in salivary pH may occur rapidly, as when highly acidic material is taken into the mouth, or relatively gradually, as when salivary flora metabolize refined sugar and other carbohydrates. Owing to the constant flow of salivary fluid into the mouth, the aforementioned gradual pH changes seldom occur in saliva contacting fully exposed enamel surfaces. Gradual changes frequently occur, however, in so-called "small spaces" or "salivary retention areas", i.e., areas of contact between adjacent teeth or between dental or orthodontic appliances and teeth, small pits or grooves in enamel surfaces, and at the site of adherence of dental plaque.

As a result of experimental work by the inventor and his co-workers, it has long been accepted that hydrostatic forces affecting fluids in these confined spaces substantially preclude the physical displacement of retained saliva by ordinary parotid fluid flow. Bacterial fermentation of sugars and the like is thus permitted to proceed in these spaces essentially undisturbed and can result in dramatic pH drops in retained saliva within a matter of minutes or hours depending upon the bacterial count within the narrow space, even though salivary flow in the mouth is altogether normal. Such drops in pH, as noted above, provide an environment conducive to selective dissolution of enamel.

The cariogenicity of fluids retained in salivary retention areas is further enhanced by osmotic forces extant in the oral cavity. Oral intake of foods having soluble refined sugars and other cariogenic substances will, of course, result in enhancement of food supplies for bacteria in salivary retention areas. Despite the general inability of flowing saliva to displace retained saliva, osmotic differentials between "trapped" saliva and saliva containing dissolved sugars will result in migration of these bacterial nutrients into salivary retention areas. To the extent that there is a tendency for dissolved sugars and the like to migrate from salivary retention areas across hydrostatic force barriers and into fresh flowing saliva (thereby effecting a depletion of bacterial food supplies) so also is there a tendency for retained fluids to be similarly depleted of their "normal" complement calcium and phosphate ions because the ions migrate along with the osmotically active substances. This results in an amplification of unsaturation of retained saliva with respect to these ions, so that fluids of even moderately low pH will have more extensive cariogenic effect. In sum, both hydrostatic and osmotic force effects in the mouth tend to create a medium in the salivary retention areas which is particularly conducive to carious degradation of enamel. Indeed, it is precisely in these areas that the highest incidence of dental caries is encountered. Similarly, the most highly cariogenic foodstuffs have been found to be acidic fluids having high concentrations of refined sugars in a dissolved state.

Review of prior art developments within the context of the above analysis of events taking place in the oral cavity provides an explanation for the very limited successes that have been achieved in the art. Simply put, none of the prior proposals have adequately taken into consideration and accommodated for the dynamic hydrostatic and osmotic forces at the localized level of salivary retention areas within the mouth. Apart from bactericidal compositions which inhibit bacterial propagation upon transport of active agents into these areas, none of the prior art localized treatments have been designed to mitigate the adverse effects of bacterial proliferation in terms of decreased pH and consequent calcium and phosphate ion "imbalances". Further, no prior art methods and materials have had as their focus the "neutralization", prior to oral intake, of the ion-imbalancing, cariogenic effects of foodstuffs containing refined sugars and other soluble carbohydrates.

SUMMARY

In one aspect, the present invention provides novel methods and materials for treating the mouth to counteract the deleterious effects of cariogenic substances present in salivary retention areas. An embodiment of this aspect of the invention is an aqueous mouth rinse comprising either a soluble source of calcium ions or a source of phosphate ions together with a non-toxic, osmotically active substance providing for transport of the selected ions into salivary retention areas. The quantity of selected ions in the rinse is such that there will be supplied to the salivary retention areas sufficient ions to exceed the pH dependent product of calcium and phosphate (as total phosphorous) ion concentrations at which dissolution of enamel will not take place.

Another aspect of the invention provides novel methods for treating cariogenic substances such as refined sugar and acidic foodstuffs to "neutralize" their cariogenic effects. In one embodiment, mixtures of refined sugar and a selected, soluble, calcium or phosphate salt are prepared e.g., by solution and recrystallization. The concentration of calcium or phosphate ion source in the sugar mixture is such as will supply salivary retention areas with sufficient ions to exceed the above-noted ion concentration product. Sugar treated in this manner may then be substituted for non-treated refined sugar in foodstuffs. It is of substantial importance that the calcium or phosphate ion source be as rapidly soluble in saliva as the sugar so that the protective ions will migrate to salivary retention areas as rapidly as the sugar.

In another embodiment highly cariogenic foodstuffs such as acidic, sugar-containing soft drinks are treated to augment calcium and/or phosphate ion concentrations so that acid or bacterial nutrient materials transported into salivary retention areas will be accompanied by calcium and/or phosphate ions in amounts sufficient to prevent dissolution of enamel despite rapid or gradual increments in acidity of the retained fluids.

Other aspects and advantages of the present invention will become apparent upon consideration of the following detailed description.

DETAILED DESCRIPTION

As indicated above, the present invention has its origins in prior work by the inventor and his co-workers concerning two distinct and heretofore unrelated phenomena, i.e., (1) the relative stability of the ionic constitution of fluids within salivary retention areas of the mouth, and (2) the variable cariogenicity of acid solutions comprising calcium and phosphate ions in varying relative concentrations, as demonstrated by in vitro studies.

The more pertinent of the inventor's early publications concerning the relative stability of fluids in salivary retention areas include *J.D. Res.*, 29, No. 3, pp. 285–90 (1950); *J.D. Res.*, 45, No. 5, 1499–1510 (1966) and *J.D. Res.* 28, pp. 379–390 (1949). Briefly put, the inventor observed and reported that transport of ions and molecules by diffusion into narrow spaces (such as salivary retention areas) from bulk solutions (such as flowing saliva) is very slow. Significantly, the inventor noted that rapid, mass transport of a solute from bulk solutions into narrow spaces occurs if the osmolality and/or density of the former is greater than that of the latter. Consistent with the above, it was further noted that (1) the habitual ingestion of concentrated fermentable sugars produces frequent osmolality and density changes in bulk oral saliva with resultant rapid and repeated conveyance of all constituents into the microvolume salivary retention areas; and (2) ingestion of highly salted foods produces similar changes and similar conveyance of all constituents (even low concentrations of carbohydrates) into salivary retention areas.

Within a different scientific context, the inventor and his co-workers exhaustively investigated changes in enamel brought about by carious degradation. Model in vitro systems were constructed to simulate cariogenic environments so that the effects of proposed cariostatic agents could be ascertained and quantified. Among the earliest publications relating to these studies was Coolidge, et al., *Oral Surg., Oral Med., & Oral Path.*, 8, No. 11. pp. 1204–1210 (1955) wherein it was disclosed that clinically produced caries-like changes in enamel could be substantially duplicated artificially using inorganic acid solutions containing both calcium and phoshate ions. Enamel changes brought about by, e.g., hydrochloric acid alone, do not resemble in vivo caries formation. The cariogenicity of an acid solution of a given pH was shown to be dependent upon the product of the concentrations of calcium and phosphate (expressed as total phosphorous) and effectively independent of the absolute concentrations of each of the ions. More particularly, an essentially linear correlation was shown to exist between the ion concentration product and cariogenicity of acid solutions having increasing pH's.

Recent basic research by the inventor into the effect of various concentrations of fluorine on mitigating the cariogenicity of acid solutions applied in vitro provided most remarkable results. In general, these studies revealed that almost infinitismally small concentrations of fluorine ion (e.g., on the order of 0.012 parts per million) were needed to substantially depress the cariogenicity of standardized "half-saturated" acidic test solutions prepared by saturating the organic and inorganic acid solutions with the most soluble of the calcium phosphates (calcium orthophosphate) and then doubling their volume with distilled water. Such "half-saturated" acid solutions had earlier been determined imperically to be highly cariogenic. The remarkably low fluorine concentrations necessary to render such test solutions non-cariogenic closely approximated those which have been reported to be extant in saliva of persons regularly ingesting fluoridated water. As such, the experimental studies appeared to provide a most promising vehicle for the objective determination of the true mechanism of action of fluorine as a cariostatic agent.

In order to ascertain the precise parameters of the fluorine addition phenomenon whereby cariogenic fluids were rendered non-cariogenic, numerous experimental modifications of model cariogenic solutions were made. Solutions of known cariogenic foodstuffs were subjected to calcium and phosphate ion augmentation (to render the solutions closely similar to those model systems which generate caries-like changes) and tested for the effects on in vitro cariogenicity of small quantities of fluorine ion. Studies were also conducted wherein saliva was provided with fermentable refined sugars and then supplemented with varying concentrations of calcium, phosphate and fluorine ions before use in test systems.

The results of these tests varied quite inconsistently, with the fluorine-free "control" solutions frequently providing to be as non-cariogenic as "test" solutions containing fluorine in concentrations which were earlier believed to be the minimum necessary for cariostatic activity. Exhaustive repetitions of in vitro analyses were carried out. The results increasingly indicated that, apart from the rather inexplicable cariostatic effects of minor quantities of fluorine on cariogenic test media, the relatively elementary process of augmenting either the calcium or phosphate ion content of the otherwise cariogenic test fluids (especially saliva) tended to render them non-cariogenic.

The calcium or phosphate ion augmentation necessary to neutralize an otherwise cariogenic test fluid was found to be essentially independent of absolute ion concentration but (just as in the case of applicant's much earlier in vitro work) dependent rather upon the product of calcium and phosphate ion concentration. Also, the minimum ion product required was found to vary essentially linearly in relation to pH of the solution. Further, it was determined that such cariostatic concentrations of the ions could be quite effectively delivered to salivary retention areas in the mouth by combining them with osmotically active substances and thereby facilitating migration of the ions from fluids in the mouth across hydrostatic barriers.

The following examples illustrate practice of the invention in its many aspects. As used herein the term "cariogenic substance" shall mean and include materials which promote the dissolution of dental enamel. The term, therefore includes, but is not limited to, acidic solutions and substances which, when contacted with saliva, tend to acidify saliva. Also included are materials providing nutrients for oral flora and consequently enhancing the proliferation of the flora and the acidification of the floral growth medium. Comprehended by this definition, therefore, are acidic foodstuffs, medications and even mouth rinses, as well as refined sugars, carbohydrates and the like which are capable of providing soluble nutrients for floral growth. Carbohydrates comprehended as cariogenic substances treatable according to the invention include polysaccharides (which are broken down by salivary enzymes to di- and monosaccharides) as well as disaccharides (maltose, sucrose, lactose and the like) which are broken down in saliva to monosaccharides such as dextrose, levulose, galactose and the like.

As used herein, the term "osmotically active substance" shall mean and include water soluble or miscible substances which will rapidly migrate across hydrostatic barriers from volumes of high concentration to volumes of low concentration. Comprehended by this definition are soluble inorganic salts such as sodium chloride, potassium chloride, sodium sulfate and the like, soluble carbohydrates such as sucrose, glucose, fructose and the like and soluble sorbitol, mannitol, xylitol, glycerine and similar non-toxic polyhydric alcohols. Preferred is d-sorbitol which is itself known to be non-cariogenic when added to saliva and which, unlike sodium chloride, is tasteless and will not contribute unnecessary ions to a treatment solution.

According to one aspect of the present invention, cariogenic substances are treated to include soluble sources of calcium or phosphate ions in substantially uniform distribution. Substances so treated have diminished cariogenic effects because their solvation in saliva and subsequent transport to salivary retention areas will be uniformly accompanied by solvation and transport of calcium or phosphate ions in such quantities as will effectively "neutralize" the effects of pH drops in these areas. Put another way, a material which is cariogenic by virtue of directly or indirectly participating in the lowering of pH in salivary retention areas is rendered non-cariogenic by treatment to incorporate enough of either a calcium or phosphate ion source to keep the acidic medium from dissolving the tooth enamel.

The efficacy of the treatment methods of the invention is most suitably demonstrated by the results of in vitro testing for the cariogenic effects of solutions containing equal quantities of treated and non-treated cariogenic substances.

EXAMPLE 1

This example provides the experimental procedure employed to demonstrate utility of the present invention in prevention of carious degradation of teeth. The methodology generally consists of exposing portions of a tooth surface to contact with "test" and "control" solutions of specified character and then periodically observing and recording changes in the tooth surface. More specifically, for any given procedure, tooth segments subjected to test and control solutions were obtained from the same tooth by the simple expedient of dividing a single tooth into a desired number of segments. Tooth segments so obtained were then mounted on a small block of hard wax. Enamel surfaces were covered with dental sticky wax (Kerr Dental Mfg. Co.) except for a 2 mm × 4 mm rectangular "window" which was left exposed for contact with the solutions. Unless otherwise indicated, contact of the tooth surface with the solutions was carried out by immersing in a given volume of the solution under "incubating" temperature conditions of 37° C.

EXAMPLE 2

Sucrose is treated according to the invention by dissolving in a suitable solvent, then adding to the solution so formed the desired quantity of a water soluble source of calcium ions or phosphate ions, and finally recrystallizing the resulting solution. The preferred solvent for use in such treatment is water. While a variety of soluble sources of calcium ions such as calcium gluconate, calcium proprionate, calcium gluceptate, and calcium chloride may be employed, and while calcium lactate is somewhat preferred on the basis of cost, solubility in water and palatability the benefits of sucrose treatment according to the invention are best obtained when the source of calcium ions is as rapidly soluble in saliva as sucrose. Thus calcium gluceptate, calcium chloride and especially calcium propionate are preferred as additives for sucrose. Calcium propionate is reported to dissolve in water in the amount of 55.8 grams per 100 ml water at 100° C. Similarly, while potassium phosphate and ammonium phosphate can provide suitable sources of phosphate ions, sodium phosphate ($Na_2HPO_4 \cdot 12H_2O$) is preferred.

The above-noted solution and recrystallization process is much preferred to, for example, the dry mixing of sucrose with the selected ion source because it provides for greater uniformity of distribution.

Cariogenic substances in aqueous form may be treated by simple addition and mixing of the soluble ion source.

EXAMPLE 3

This example illustrates variations in the rate of solubility of calcium ion sources and phosphate ion sources in water and filtered saliva.

A first series of rate of dissolution studies was carried out by placing a given quantity of selected substance evenly on the bottom surface of a dry beaker. Ten milliliters of water was added to the beaker without stirring. The time required for the entire quantity of solute to disappear was noted. The results are set out in Table I below.

TABLE I

| Substance | Quantity (grams) | Time Required For Dissolution (seconds) |
|---|---|---|
| Calcium lactate | 0.10 | 2100 |
| Calcium gluconate | 0.10 | 1900 |
| Calcium propionate | 0.10 | 60 |
| Calcium gluceptate | 0.10 | 5 |
| Calcium glycerophosphate | 0.10 | 1200 |
| Calcium chloride | 0.10 | 15 |
| $Na_2H\ PO_4.12H_2O$ | 0.10 | 480 |
| Table sugar | 1.00 | 1200 |
| Table sugar | 0.05 | 40 |
| Calcium lactate | 0.0013 | 65 |
| Calcium propionate | 0.0009 | 10 |

A second series of dissolution studies was carried out according to the procedure noted immediately above, but using 10 ml of human saliva filtered through No. 41 Whatman filter paper. The results are set out in Table II below.

TABLE II

| Compound | Quantity (grams) | Time Required For Dissolution (seconds) |
|---|---|---|
| Table sugar | 0.05 | 85 |
| Calcium lactate | 0.0013 | 360 |
| Calcium propionate | 0.0009 | 15 |
| Calcium gluceptate | 0.001 | 12 |

The above results of rate of solubility serve to amplify the previously-noted remarks with respect to relative rates of solution of cariogenic solids and sources of calcium ions or phosphate ions. If, for example, a source of calcium ions employed to treat sucrose according to Example 2 is one which is less rapidly soluble in saliva than sucrose, then it is much less likely to be effective in diminishing the cariogenicity of the sugar. During a relatively brief amount of time following oral intake of the treated sugar, the sucrose would rapidly dissolve and be rapidly transported into salivary retention areas by the osmotic forces noted above. If the calcium source is less rapidly soluble then calcium ions will not effectively be transferred to these areas along with the sugar. This aspect of the invention serves to explain the absence of consistent results in those prior experimental processes wherein some attempt was made to incorporate calcium-containing, but phosphate-free compounds in cariogenic solid diets. While the relative rate-of-dissolution "defects" of calcium ion sources could be modified somewhat by substantially increasing the quantities involved, the adverse effects of early dissolution and migration of a cariogenic material to salivory retention areas are best dealt with by use of a rapidly soluble ion source as a treating agent. In aqueous solutions according to the invention, rate of dissolution of calcium or phosphate ion sources does not have similar significance, it being necessary only to establish the proper overall concentration of effective ions in the solution (e.g., as indicated below, at least about 3.25 mg calcium ion or about 1.08 mg phosphate ion per gram of sucrose).

EXAMPLE 4

This example illustrates the salutary effects of treatment of sucrose with a soluble source of calcium ions. A total of fifteen experimental procedures (involving 35 tooth specimens) were carried out according to the methodology of Example 1. In each instance the control solutions employed consisted of fresh human saliva to which was added sucrose (supplied as table sugar) in a quantity sufficient to develop a 10% by weight solution. Test solutions were identical to controls except for their including sucrose which was either pre-treated with a calcium ion source (e.g., by solution and re-crystallization as in Example 2) or treated in situ by the concurrent addition of the sucrose and calcium ion source to the saliva. In two instances the test solution also contained a source of fluoride ions. All initial solution pH values were approximately 7.0 and dropped rather uniformly over the period of observation as a result of bacterial fermentation.

Table III below summarizes the data obtained in the course of the 14 procedures. In the Table, tooth specimens are designated either as control ("C") or test ("T") specimens. The various test and control solutions are designated according to the following abbreviations:
  A. Saliva plus sucrose.
  B. Saliva plus sucrose plus calcium lactate plus a source of fluoride ion in a quantity sufficient to develop a fluoride ion concentration of about 0.10 p.p.m. or less.
  C. Saliva plus sucrose plus calcium lactate.
  D. Saliva plus sucrose plus calcium gluconate.
  E. Saliva plus sucrose plus calcium propionate.
  F. Saliva plus sucrose plus calcium chloride.

Total quantities of calcium ion supplied to a given volume of solution are given in terms of mg/ml, based on the molecular weight of the reagent employed. As one example, a value of "390 mg/ml" indicates that 30 ml of saliva test solution contained, in addition to the quantity of calcium ion naturally present, 390 mg of calcium ion. Such a quantity could be provided by addition of 3 grams of calcium lactate (supplied as a reagent in hydrated form, M.W. 308.22).

Enamel surface changes observed are designated as follows:

TABLE III

| Procedure No. | Specimen | Solution | Supplemental [Ca] | Final pH | Time in Solution/Surface Change | | | | |
|---|---|---|---|---|---|---|---|---|---|
| 124 | C | A | 0 | 3.5 | 21 hrs/+; | 41 hrs/+; | 2 days/++; | 3 days/++. | |
|  | T | B | 390 mg/30 ml | 3.7 | 21 hrs/O; | 41 hrs/O; | 2 days/O; | 3 days/O | |
| 126 | C | A | 0 | 3.5 | 12 hrs/⊕; | 36 hrs/+; | 60 hrs/++; | 4 days/++; | 5 days/++. |
|  | $T_1$ | C | 390 mg/30 ml | 3.7 | 12 hrs/O; | 36 hrs/O; | 60 hrs/O; | 4 days/⊕; | 5 days/⊕. |

TABLE III-continued

| Procedure No. | Specimen | Solution | Supplemental [Ca] | Final pH | Time in Solution/Surface Change | | | | |
|---|---|---|---|---|---|---|---|---|---|
|  | $T_2$ | B | 390 mg/30 ml | 3.7 | 12 hrs/O; | 36 hrs/O; | 60 hrs/O; | 4 days/$\oplus$ | 5 days/$\oplus$. |
| 127 | C | A | 0 | 3.4 | 24 hrs/$\oplus$; | 49 hrs/+; | 4 days/++; | 6 days/++; | 9 days/++. |
|  | T | C | 390 mg/30 ml | 3.6 | 24 hrs/O; | 49 hrs/O; | 4 days/O; | 6 days/O; | 9 days/O. |
| 129 | C | A | 0 | 3.5 | 19 hrs/$\oplus$; | 28 hrs/+; | 42 hrs/++. | | |
|  | $T_1$ | C | 6.5 mg/20 ml | 3.9 | 19 hrs/O; | 28 hrs/O; | 42 hrs/$\oplus$. | | |
|  | $T_2$ | C | 3.25 mg/20 ml | 3.8 | 19 hrs/O; | 28 hrs/$\oplus$; | 42 hrs/+. | | |
| 132* | $C_{1-10}$ | A | 0 | 3.6 | 24 hrs/$\oplus$; | 48 hrs/+; | 54 hrs/+; | 65 hrs/++. | |
|  | $T_{1-10}$ | C | 16.25 mg/50 ml | 3.9 | 24 hrs/O; | 48 hrs/O; | 54 hrs/O; | 65 hrs/O to $\oplus$. | |
| 134 | C | A | 0 | 3.6 | 21 hrs/$\oplus$; | 28 hrs/+; | 41 hrs/+. | | |
|  | T | C | 6.5 mg/20 ml | 4.0 | 21 hrs/O; | 28 hrs/O; | 41 hrs/O. | | |
| 135 | C | A | 0 | 3.7 | 4 hrs/$\oplus$; | 11 hrs/+; | 24 hrs/+. | | |
|  | T | C | 6.5 mg/20 ml | 3.8 | 4 hrs/O; | 11 hrs/O; | 24 hrs/O. | | |
| 136 | C | A | 0 | 3.4 | 23 hrs/$\oplus$; | 40 hrs/+; | 48 hrs/+. | | |
|  | T | D | 4.46 mg/20 ml | 3.4 | 23 hrs/O; | 40 hrs/O; | 48 hrs/$\oplus$. | | |
| 138 | C | A | 0 | 3.4 | 5 hrs/+. | | | | |
|  | T | D | 4.46 mg/20 m; | 3.4 | 5 hrs/$\oplus$. | | | | |
| 139 | C | A | 0 | 3.4 | 23 hrs/+; | 28 hrs/+; | 47 hrs/++. | | |
|  | T | D | 6.5 mg/20 ml | 3.6 | 23 hrs/O; | 28 hrs/O; | 47 hrs/$\oplus$. | | |
| 140 | C | A | 0 | 3.3 | 19 hrs/+; | 47 hrs/+; | 64 hrs/++; | 89 hrs/++. | |
|  | T | E | 6.5 mg/20 ml | 3.6 | 19 hrs/O; | 47 hrs/O; | 64 hrs/O; | 89 hrs/O. | |
| 142 | C | A | 0 | 3.8 | 3 days/$\oplus$; | 4 days/+; | 4 days, 17 hrs/++. | | |
|  | T | C | 6.5 mg/20 ml | 4.3 | 3 days/O; | 4 days/O; | 4 days, 17 hrs/O. | | |
| 149 | C | A | 0 | 3.5 | 6 hrs/$\oplus$; | 29 hrs/+; | 47 hrs/++; | 72 hrs/++. | |
|  | T | F | 6.5 mg/20 ml | 3.6 | 6 hrs/O; | 29 hrs/O; | 47 hrs/O; | 72 hrs/O. | |
| 150* | $C_{1-10}$ | A | 0 | 3.4 | 26 hrs/$\oplus$; | 36 hrs/+; | 47 hrs/+; | 61 hrs/+ to ++. | |
|  | $T_{1-10}$ | C | 16.25 mg/50 ml | 3.5 | 26 hrs/O; | 36 hrs/O; | 47 hrs/O; | 61 hrs/O to $\oplus$. | |

*10 specimens each procedure; surface changes noted in terms of average values among the 10 specimens.
O = no action
$\oplus$ = white spots in isolated zones
+ = caries-like alteration of total exposed surface
++ = increased caries-like alteration, surface can be indented with a steel probe.

The results of the fourteen procedures reported in Table III effectively demonstrate that carious degradation of enamel surfaces such as brought about by salivary bacterial fermentation of sucrose is precluded by the presence of calcium ions. Depending on the quantity of soluble source of calcium ion supplied, caries-like action was inhibited for from 28 hours to 9 days. Of the calcium ion source materials employed, calcium lactate showed the most consistent protective effects at low doses of about 0.325 mg/ml [Ca] (reported e.g., as 6.5 mg/20 ml). At lower concentrations, such as $T_2$ in procedure 129 (0.167 mg/ml) and T in procedure 138 (0.223 mg/ml), protective effects were noted, but not for as extensive periods of time. A ratio of 3.25 mg calcium ion per gram of sucrose can be achieved by augmentation of each gram of sucrose with, e.g. about 25.0 mg calcium lactate or 36.36 mg calcium gluconate or 16.36 mg calcium propionate, and the like.

It is appropriate to note that augmentation of the test solutions with fluorine in low dosages did not appreciably enhance the protection donated by the calcium augmentation. Procedures 134 and 135 were carried out with saliva from persons living in areas not supplied fluoridated water. Protection was obtained despite the absence of systemic or added fluorine, a result even further obscuring the precise role of fluorine in prevention of caries. Similar good results attend augmentation of cariogenic saliva/dextrose, saliva/maltose and saliva/cornstarch mixtures with soluble sources of calcium.

EXAMPLE 5

In order to verify that the above-noted protective effects were exclusive to calcium ions, rather than other cations, a procedure similar to those of Example 4 was carried out using magnesium chloride in the place of, e.g., calcium chloride. A saliva solution containing 10 percent by weight of table sugar was prepared. To a 20 ml "test" portion was added 39.157 mg of magnesium chloride. No differences whatever were noted in the rate of formation of caries-like lesions on the test and control tooth segments. In both test and control solution, the total exposed surface of the tooth was altered in a caries-like manner within 24 hours.

EXAMPLE 6

This example illustrates the salutary effects of treatment of sucrose with a soluble source of phosphate ions. A total of five procedures (involving 6 tooth specimens) were carried out according to the methodology of Example 1. In each instance the control solutions consisted of fresh human saliva to which was added sucrose (supplied as table sugar) in a quantity sufficient to develop a 10% by weight solution. Test solutions were identical to controls except for their including sucrose which was either pre-treated (e.g., by solution and re-crystallization as in Example 2) or treated in situ by the concurrent addition of the sucrose and monohydric sodium orthophosphate ($Na_2HPO_4.12H_2O$) to the saliva. All initial solution pH values were approximately 7.0 and dropped rather uniformly over the period of incubation.

Table IV below summarizes the data obtained in the course of 5 procedures, with "T" and "C" designating test and control tooth segments respectively; "A" designating a 10% sucrose/saliva solution and "B" designating the same solution to which sodium phosphate has been added. Quantities of phosphate ion added are expressed in mg/ml. Enamel surface changes are designated in the same manner as in Table III.

TABLE IV

| Procedure No. | Specimen | Solution | Supplemental [P7] | Final pH | Time in Solution/Surface Change | | | |
|---|---|---|---|---|---|---|---|---|
| 128 | C | A | 0 | 3.5 | 1 day/⊕; | 1½ days/++ | | |
|  | T | B | 17.29 mg/20 ml | 6.0 | 1 day/O; | 1½ days/O | | |
| 130 | C | A | 0 | 3.5 | 21 hrs/+; | 46 hrs/++; | 3 days/++ | |
|  | T | B | 4.34 mg/20 ml | 3.8 | 21 hrs/O; | 46 hrs/O; | 3 days/⊕ | |
| 131 | C | A | 0 | 3.5 | 22 hrs/⊕; | 48 hrs/+; | 2 days/++ | |
|  | T | B | 2.162 mg/20 ml | 3.5 | 22 hrs/O; | 48 hrs/O; | 2 days/⊕ | |
| 137 | C | A | 0 | 3.5 | 21 hrs/⊕; | 34 hrs/+; | 44 hrs/++; | 50 hrs/++ |
|  | T | B | 2.162 mg/20 ml | 3.8 | 21 hrs/O; | 34 hrs/O; | 44 hrs/O; | 50 hrs/⊕ |
| 144 | $C_{1-2}$ | A | 0 | 4.4 | 34 hrs/+; | 54 hrs/+; | 70 hrs/++ | |
|  | $T_{1-2}$ | B | 2.162 mg/20 ml | 5.3 | 34 hrs/O; | 54 hrs/O; | 70 hrs/O | |

The results of the five procedures reported in Table IV effectively demonstrate that carious degradation of enamel surfaces such as brought about by salivary bacterial fermentation of sucrose is precluded by treatment to provide a soluble source of phosphate ions. Protective effects were achieved at low phosphate ion doses of about 0.108 mg/ml (reported as 2.162 mg/20 ml). Such augmentation of sucrose with phosphate ion can be achieved by addition, per gram of sucrose treated of, e.g., 12.49 mg monohydric sodium orthophosphate or 4.61 mg monohydric ammonium phosphate or 6.07 mg monohydric potassium phosphate or the like.

The data set forth in Tables III and IV establish that a cariogenic substance such as sucrose (provided as table sugar) can be rendered effectively non-cariogenic by mixture with approximately 2.5 weight percent of a soluble source of calcium ions or a soluble source of phosphate ions, with the sources preferably having rates of dissolution equal to or greater than that of sucrose.

While not intended to be binding upon practice of the invention, it is proposed that the avoidance of caries-like action in sucrose/saliva "test" solutions is due in part to the binding of calcium and phosphate ions to salivary protein when the saliva is at or near pH 7.0. Certain of applicant's prior publications have established with substantial certainty that calcium and phosphate ions are reversibly bound to salivary albumins, globulins, mucin and the like. See, e.g., Lightfoot, et al., *J.D. Res.*, 40, pp. 311–313 (1961). These proteinaceous materials have differing isoelectric pH's in the range of 6.0 to about 3.0 and, as the pH in the saliva test solutions drops, it is probable that these "stored" ions are gradually released into the salivary fluids to inhibit dissolution of enamel surfaces.

It is significant to note that augmentation of a cariogenic material with both a soluble source of calcium ions and phosphate ions is not expected to be effective in prevention of dental caries. A first drawback for such procedures—which essentially mirror those unsuccessful procedures of the prior art—is the rapid precipitation of insoluble calcium phosphate salts upon the solvation of the calcium and phosphate ion sources by saliva. The calcium and phosphate ions simply will not reach the salivary retention areas along with the dissolved cariogenic material. It is also worthy of note that experimental procedures, generally patterned after those of Examples 4 and 6 and wherein there has been an attempt to supply both calcium and phosphate ions, have provided rather poor protection against caries-like changes in tooth segments. This observation is not susceptible to easy explanation, especially in view of the "closed" system employed in the in vitro test procedure. It appears, however, that once the calcium and phosphate ions are lost to the system by precipitation at close to neutral pH, they remain unavailable despite subsequent drops in pH which would ordinarily be expected to cause dissolution of the precipitates.

EXAMPLE 7

This example illustrates the salutary effects of treatment of various commercially available foodstuffs noted for their cariogenicity. In one procedure, segments of three human molars were mounted, waxed and immersed in the following solutions including two popular carbonated cola beverages (Brands "A" and "B").

| | |
|---|---|
| Solution No. 1 | 100 ml cola "A", 1 gram calcium lactate (final pH 4.5) |
| Solution No. 2 | 100 ml cola "A", 1 gram calcium lactate, sodium fluoride to a concentration of 0.10 ppm. (final pH 4.5) |
| Solution No. 3 | 100 ml. cola "A", sodium fluoride to a concentration of 0.10 ppm (final pH 3.0) |
| Solution No. 4 | 100 ml cola "A", 1 gram calcium lactate 18 minims of 20% lactic acid (final pH 4.0) |
| Solution No. 5 | Same as No. 4 plus 0.05 ppm sodium fluoride (final pH 4.0) |
| Solution No. 6 | 100 ml cola "B" (pH 3.0) |
| Solution No. 7 | 100 ml cola "B", 1 gram calcium lactate (final pH 4.5) |
| Solution No. 8 | Same as No. 7 plus 18 minims 20% lactic acid (final pH 4.0) |

Segments of the first molar were separately immersed in Solution Nos. 1, 2 and 3; the second molar in Solutions Nos. 4 and 5; the third molar in Solution Nos. 6, 7 and 8. Tooth segments in Solution Nos. 3 and 6 were noticeably etched after 2 hours immersion and 10 minutes immersion, respectively. Continued soaking in Solution No. 3 resulted in loss of surface contour of the enamel after 3 days. Similar results were brought about by Solution No. 6 in as little as two days. All other tooth segments had remained unchanged when the test was concluded after 4 days. Substantially identical results were observed in similar tests involving fruit flavored soft drinks augmented by addition of dicalcium phosphate.

In another procedure, test and control saliva solutions were prepared by mixing about 45 ml of saliva with about 5.0 grams of crushed candy drops. The stirred mixture was passed through a cheese cloth filter to remove large particles. One half of the saliva/candy solution was separated and augmented 0.05 grams of calcium lactate and both portions were incubated for about 26 hours at 37° C. Both solutions then had a pH of about 3.8. Split tooth specimens were then allowed to incubate in the solutions. Within 13 hours, slight caries-like action was observed on the control tooth and after 24 hours the total surface of the control tooth surface was affected. The test solution tooth showed no changes over the same period of time. Operating on the assumption that 5 grams of the crushed candy drops contained about 4.5 grams of sucrose, it is once again demonstrated that approximately 2.5 weight percent of a soluble source of calcium ions proved sufficient to inhibit the cariogenic effects of the sucrose.

The following examples illustrate the preparation and effectiveness of mouth rinses according to the present invention.

EXAMPLE 8

The following mouth rinse solutions were prepared:

A. A 10% solution of d-sorbitol in water and further including 3% calcium lactate, food coloring and either potassium sorbate or ethanol as a preservative;

B. A 20% solution of calcium propionate in water;

C. A 10% solution of calcium propionate in water; and,

D. A 10% solution of d-sorbitol in water and further including 2% $Na_2HPO_4.12H_2O$, food coloring and either potassium sorbate or ethanol as a preservative.

The following saliva/sugar solutions were prepared:

1. A 5% solution of table sugar in saliva; and,
2. A 10% solution of table sugar in saliva.

The 5% saliva/sugar solution caused enamel changes on an incubated tooth segment within less than 24 hours and the enamel surfaces could be indented with a steel probe by the time 46 hours of incubation had passed.

Tooth segments incubated in equal volume mixtures of either of the 5% or 10% saliva/sugar solutions and one of the mouth rinse solutions A through D showed no surface changes whatever for periods of from two to ten days. These results establish that delivery of suitable quantities of either calcium or phosphate ions in the form of a mouth rinse will inhibit the adverse effects of sugar within saliva. It should be noted that calcium propionate appeared to substantially reduce the extent of decrease of pH upon incubation. In rinse solutions A and D, the calcium or phosphate ion sources are accompanied by d-sorbitol to assist in the mass transfer of selected ions from the mouth to saliva trapped in salivary retention areas. In rinse solutions B and C, the propionate serves both as a source of calcium and osmotic agent for delivery of calcium ions to the "target" areas.

EXAMPLE 9

In order to determine the readiness with which the rinses of Example 8 would effect transfer of calcium ion reserves into salivary retention areas, the following procedure was carried out. Four microscopic slides were assembled in pairs separated by a 1 mm. space, providing two "open" sides 10 mm. long and 1 mm. wide for each pair. The "chamber" between slides was filled with a 5 percent saliva/sucrose mixture. One pair of slides was immersed in the mouth rinse of Type A of Example 8 without the flavoring agent but with several drops of methylene blue dye. The other slide pair was immersed in a water solution of 5 percent sucrose and the blue dye. Colored material completely filled the space in the mouthrinse-soaked pair of plates within 8 seconds, while colored material from the aqueous sucrose solution did not completely penetrate the space between plates even after over 3 minutes of soaking. In still another procedure a solution of saliva and 5% sugar plus a few drops of methylene blue was used to fill the chamber between a pair of plates as described above. The plates were immersed in a 3% solution of calcium lactate in water. The average time required for the blue color to disappear from the chamber was 8 minutes (three trials of 6, 8 and 10 minutes). The procedure was repeated, with immersion of the chamber in a 3% calcium lactate solution which additionally contained 10% di-sorbitol. The color in the chamber disappeared in approximately 9 seconds (three trials of 8, 6 and 10 seconds), demonstrating rapid "delivery" of caries inhibiting calcium ions to small spaces such as salivary retention areas.

As noted above, it is a principal object of the present invention to provide for an inhibition of carious degradation of tooth enamel in those parts of the mouth which are most highly susceptible thereto, i.e., the salivary retention areas. To accomplish this object, cariogenic substances are augmented with either a soluble source of calcium ion or a soluble source of phosphate ions so that upon transparent of the cariogenic material to such areas as a dissolved component in saliva, there will be an accompanying transport of "reserve" quantities of calcium ions or phosphate ions. The presence of such reserves in saliva retained in salivary retention areas serves to preclude tooth enamel dissolution if the acidity of the retained saliva rises to as much as pH 2.5 or less. As a practical matter, salivary bacterial proliferation ceases at about this level of acidity.

As further noted above, applicant has discovered that, so long as the acidic salivary solution in contact with the tooth contains at least a minor quantity of either calcium ions or phosphate ions, protection can be obtained solely by augmentation of the other ion. Put another way, protective effects are obtained at any given pH irrespective of the relative ratios of calcium ions to phosphate ions, provided that a suitable product of such concentration is obtained. "Normal" saliva generally contains about 0.058 mg/ml calcium and about 0.168 mg/ml phosphate.

In order to illustrate this discovery, a series of test solutions of varying pH's was prepared using hydrochloric acid. Solutions were augmented with a phosphate ion source ($Na_2HPO_4.12H_2O$) and a calcium ion source (calcium lactate) in varying absolute concentrations. Applicant found that dissolution of enamel was inhibited when calcium ion to phosphate ion ratios ($Ca/P_T$) varied from as low as about 0.066 to as high as about 4.223 so long as the required solution product of calcium ion times phosphate ion ($[Ca] \times [P_T]$, expressed in mg/ml) was achieved. The required solution product was found to be essentially linearly correlated with increases or decreases of pH ranging from about 0.5 at about pH 4.5 to about 20.0 at about pH 2.9.

Table V below sets the data obtained from eight procedures involving preparation of acidic solutions containing varying absolute quantities of calcium and phosphate ions. In each instance the ordinarily harmful effects on tooth enamel of such acidic solutions were avoided by virtue of the required, pH related, ion product having been achieved.

TABLE V

| Procedure No. | pH | Supplied [Ca] | Supplied [$P_T$] | Ca/$P_T$ ratio | [Ca] × [$P_T$] |
|---|---|---|---|---|---|
| 162 | 4.3 | 1.5075 | 0.357 | 4.223 | 0.5382 |
| 163 | 4.5 | 0.1887 | 2.86 | 0.066 | 0.5397 |
| 161 | 3.6 | 3.02 | 0.715 | 4.223 | 2.1593 |
| 160 | 3.5 | 0.3775 | 5.72 | 0.066 | 2.1593 |
| 159 | 3.4 | 0.533 | 4.29 | 0.1242 | 2.2865 |
| 165 | 3.1 | 0.755 | 11.44 | 0.066 | 8.6372 |
| 166 | 3.0 | 6.644 | 1.573 | 4.223 | 10.451 |
| 164 | 2.9 | 9.06 | 2.145 | 4.223 | 19.4337 |

Figure 1:
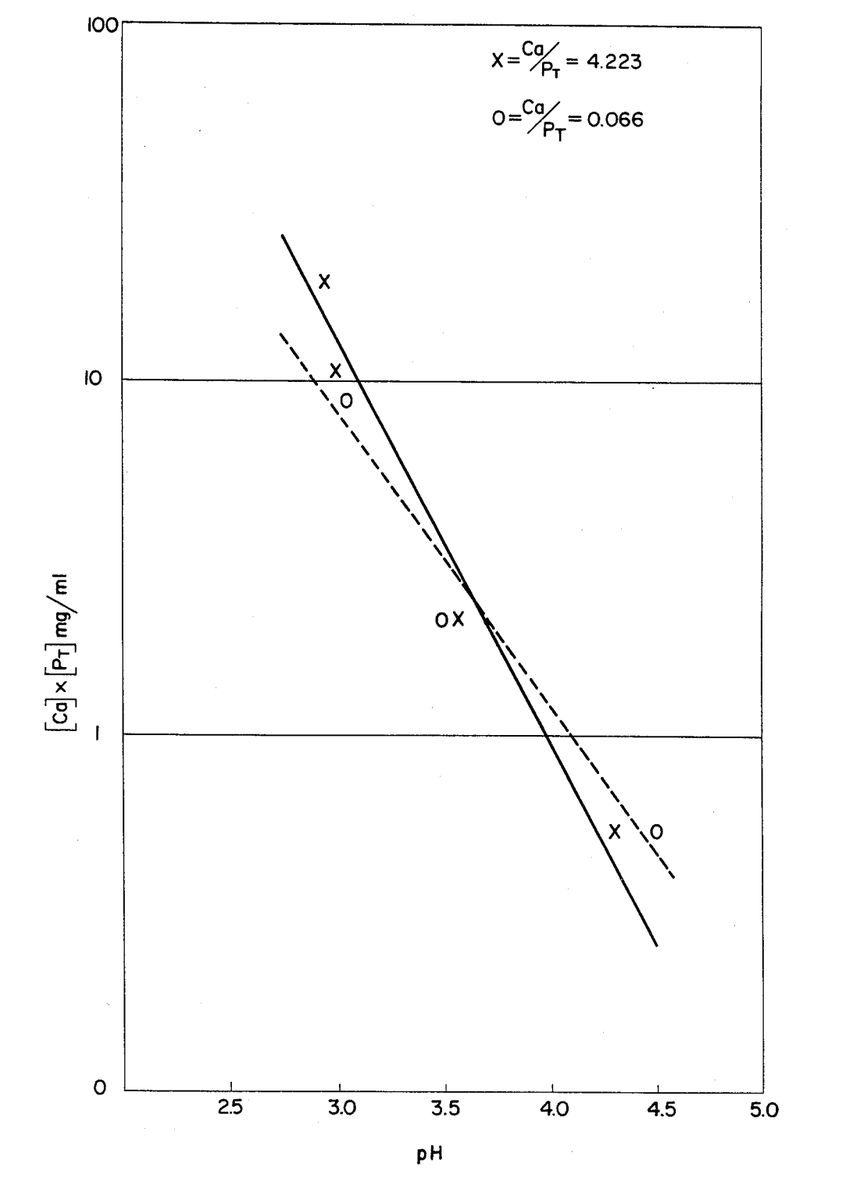

The FIGURE attached graphically illustrates the remarkable coincidence of required, pH dependent "protective" ion products for solutions having a Ca/$P_T$ ratio of 4.223 (straight line) and 0.066 (dashed line).

Consistent with the above, the invention can be seen to additionally consist providing a mouth rinse solution including: (1) a soluble source of either calcium or phosphate ions; (2) a proteinaceous material to which the "corresponding" ion is bound; and (3) an osmotically active agent. A rinse of this type would be particularly effective in treatment of patients having the condition known as xerostomia wherein salivary flow is quite low and saliva cannot be counted upon to provide any appreciable quantity of protein-bound calcium or phosphate ion. As one example, a rinse suitable for use by xerostomia patients may consist of a given volume of distilled water saturated with mucin. The solution would then be saturated with Ca.HPO$_4$.2H$_2$O. Fluorine may be added to develop a fluorine ion concentration of about 0.10 parts per million. Flavoring, coloring and antimicrobial materials may be added as desired. The quantities of calcium and phosphate ion provided in a rinse of this type would provide a Ca/$P_T$ ratio of from about 0.066 to about 4.223. A solution in which the product, [Ca]×[$P_T$] exceeded about 20 would be seen to provide protection in salivary retention areas wherein the pH might drop to 3.0 or below.

Numerous modifications and variations in the invention illustrated above are expected to occur to those skilled in the art. Consequently only such limitations as appear in the appended claims should be placed thereon.

What is claimed is:

1. A method for diminishing the cariogenicity of sucrose, said method consisting of admixing sucrose with a soluble source of calcium ions or a soluble source of phosphate ions in a quantitative weight ratio of about one part ion source to forty parts sucrose, said ion source being at least as rapidly soluble in water as sucrose.

2. The method of claim 1 wherein said admixing step comprises dissolving the sucrose and soluble source of ions in water and then evaporating the water solvent.

3. The method of claim 1 wherein the ion source is a calcium ion source and wherein the quantity of calcium ion sources employed is sufficient to provide at least about 3.25 mg calcium ion per gram of sucrose.

4. The method of claim 3 wherein said calcium ion source is calcium propionate.

5. The method of claim 1 wherein the ion source is a phosphate ion source and wherein the quantity of phosphate ion source provided is sufficient to provide at least about 1.08 mg phosphate per gram of sucrose.

6. The method of claim 5 wherein said phosphate ion source is monohydric sodium orthophosphate.

7. A method for preventing carious degradation of tooth surfaces in salivary retention areas of the mouth, said method comprising administering to the mouth a soluble source of calcium ions or a soluble source of phosphate ions in combination with an effective amount of an osmotically active agent, whereby said osmotically active agent promotes transfer of calcium ions or phosphate ions from the mouth into saliva in said salivary retention areas in quantities such that, taking into account calcium and phosphate ions already present in the saliva, the ratio of calcium ions to phosphate ions therein is from about 0.0666 to about 4.223 and the product of the concentration of calcium ions to phosphate ions therein is from about 0.5 to about 20.

8. Sucrose in crystalline form having a soluble source of calcium ions or a soluble source of phosphate ions uniformly distributed therethrough in a quantitative weight ratio of about one part ion source to forty parts sucrose, said ion source being at least as rapidly soluble in water as sucrose.

9. Sucrose in crystalline form according to claim 8 wherein the uniform distribution of soluble source of calcium ions or phosphate ions is the result of the dissolution of the sucrose and the soluble source of ions in water and the subsequent evaporation of the water solvent.

10. An aqueous solution formed by dissolving sucrose in crystalline form according to claim 8 in water.

11. Sucrose in crystalline form as in claim 8 wherein the ion source is a calcium ion source and wherein the calcium ion source employed is sufficient to provide at least about 3.25 mg calcium ion per gram of sucrose.

12. Sucrose in crystalline form as in claim 11 wherein said calcium ion source is calcium propionate.

13. Sucrose in crystalline form as in claim 8 wherein the ion source is a phosphate ion source and wherein the quantity of phosphate ion source employed is sufficient to provide at least about 1.08 mg of phosphate per gram of sucrose.

14. Sucrose in crystalline form as in claim 13 wherein said phosphate ion source is sodium orthophosphate.

15. A foodstuff containing sucrose in crystalline form having a soluble source of calcium ions distributed therethrough as a result of dissolution of the sucrose and the soluble source of calcium ions in water and the subsequent evaporation of the water solvent, said calcium ion source being at least as rapidly soluble in water as sucrose and there being present at least about 3.25 mg of calcium ions per gram of sucrose.

16. A cariostatic mouth rinse, the cariostatically active ingredients of which consist of an aqueous solution of a source of calcium ions and an osmotically active agent, the quantities of calcium ions and osmotically active agents in said mouth rinse being such that upon administration to the mouth the osmotically active agent promotes transfer of calcium ions from the mouth into saliva in salivary retention areas in the mouth in quantities such that, taking into account calcium and phosphate ions already present in the saliva, the ratio of calcium ions to phosphate ions therein is from about 0.0666 to about 4.223 and the product of the concentration of calcium ions to phosphate ions therein is from about 0.5 to about 20.

* * * * *